(12) United States Patent
Peng et al.

(10) Patent No.: US 11,768,177 B1
(45) Date of Patent: Sep. 26, 2023

(54) IONIZATION DEVICE AND METHOD OF OPERATING SAME

(71) Applicant: Molex, LLC, Lisle, IL (US)

(72) Inventors: Wenfeng Peng, North Aurora, IL (US); Mariusz Kloza, Westmont, IL (US); Miao Xu, Bolingbrook, IL (US)

(73) Assignee: Molex, LLC, Lisle, IL (US)

( * ) Notice: Subject to any disclaimer, the term of this patent is extended or adjusted under 35 U.S.C. 154(b) by 122 days.

(21) Appl. No.: 17/223,055

(22) Filed: Apr. 6, 2021

Related U.S. Application Data

(60) Provisional application No. 63/031,665, filed on May 29, 2020.

(51) Int. Cl.
    *G01N 27/66*     (2006.01)
    *G01N 33/00*     (2006.01)

(52) U.S. Cl.
    CPC ......... *G01N 27/66* (2013.01); *G01N 33/0047* (2013.01)

(58) Field of Classification Search
    CPC ............................ G01N 27/66; G01N 33/0047
    USPC .......................................................... 324/464
    See application file for complete search history.

(56) References Cited

U.S. PATENT DOCUMENTS

| | | | | | |
|---|---|---|---|---|---|
| 2,959,677 | A | * | 11/1960 | Robinson | G01N 27/66 250/382 |
| 2,968,730 | A | * | 1/1961 | Roberta | G01N 27/66 250/389 |
| 5,393,979 | A | * | 2/1995 | Hsi | G01N 27/66 250/382 |
| 5,773,833 | A | * | 6/1998 | Hsi | G01N 27/64 250/382 |
| 5,945,678 | A | * | 8/1999 | Yanagisawa | H01J 49/168 250/423 F |
| 6,734,435 | B2 | * | 5/2004 | Sun | G01N 33/0029 250/374 |
| 7,046,012 | B2 | * | 5/2006 | Dean | G01N 27/62 324/459 |
| 8,421,470 | B2 | * | 4/2013 | Kitano | G01N 30/64 324/464 |
| 10,047,437 | B2 | * | 8/2018 | Vollero | C23C 16/52 |
| 11,162,917 | B2 | * | 11/2021 | Liu | G01N 27/66 |
| 11,460,203 | B2 | * | 10/2022 | Desrochers | F24F 11/58 |

* cited by examiner

*Primary Examiner* — Christopher P McAndrew

(57) ABSTRACT

A sensor is provided for detecting small concentrations of volatile organic compounds in ambient air. The sensor has a lamp assembly and a gas sampling chamber assembly which are operatively associated. The gas sampling chamber assembly has an ionization chamber and an electrode assembly. The electrode assembly has sensing, counter and auxiliary electrodes and circuitry. The electrodes are positioned within the ionization chamber and are separated from one another. The circuitry is configured to apply a voltage difference to the sensing and counter electrodes, control an electrical potential of the auxiliary electrode to be substantially equal to an electrical potential of the counter electrode, measure/estimate a current at the sensing electrode and at the auxiliary electrode, determine a difference between the current at the sensing electrode and the current at the auxiliary electrode, and correct the current at the sensing electrode by using the difference.

20 Claims, 2 Drawing Sheets

IONIZATION DEVICE AND METHOD OF OPERATING SAME

RELATED APPLICATIONS

This application claims priority to U.S. Provisional Patent Application No. 63/031,665, filed on May 29, 2020, the entirety of which is incorporated herein by reference.

FIELD OF THE DISCLOSURE

This disclosure relates to an apparatus for the detection of gas or vapor molecules with photoionization technology and the general operation of such an apparatus.

DESCRIPTION OF RELATED ART

The concern for clean living, working and the industrial environment has increased over the recent decades. Various methods and instruments have been developed to address these concerns through accurate measurement of contaminations or pollution concentration, especially for gas contaminations. Volatile organic compounds (VOCs) remain challenging because of the colorlessness, low odor, and high reduction-oxidation reaction (aka redox) potentials in general. Photoionization detectors ("PIDs") are one of the successful solutions to tackle this difficulty because they use high energy photons to break the VOC molecules into ions and free electrons (thereby generating a plasma) and then measure the plasma current. PIDs are known for high sensitivities. They can detect gas as low as a few parts per billion (ppb), as opposed to tens or hundreds of parts per million (ppm) with other devices, e.g., infrared (IR) detectors and catalytic bead combustible gas (LEL) detectors.

The general working principle of PIDs is the measurement of ionic current which is related to the gas concentration when the gas molecules are ionized by high energy ultraviolet (UV) light. The electrons are moved into an electrical field between two electrodes and are collected on the positive electrode to form a current which is generally proportional to the gas concentration. One key part of the PID is the lamp which is usually filled with a low-pressure inert gas that emits photons in the vacuum-ultraviolet region. Salt crystals (e.g., $MgF_2$, LiF, $CaF_2$, $BaF_2$) are used as windows because common silica glasses do not transmit the short wavelength light required to ionize target VOCs. Examples of inert fill gases are helium (He), argon (Ar), krypton (Kr), or xenon (Xe). Another key part of the PID is the electrodes, which collect the plasma/ionic current in a high voltage electric field (applied on both the counter and sensing electrodes). Usually, the electrons are collected by the sensing electrode (anode, positively charged) and the resultant cations are collected by the counter electrode (cathode, negatively charged).

Ideally, the current from the sensing electrode is solely related to the gas concentration. However, in the field, the surrounding temperature and humidity of the PID sensor varies, which might result in a formation of condensation or mist outside or even inside of the sensor package. This condensation might lead to a false reading and misinterpretation of the current VOC level. The false reading might come from a leak current between the counter electrode and the sensing electrode, which is due to the formation of a conducting path as a result of condensation and other possibilities. Thus, the design to overcome such challenges like condensation or mist is critical for a robust PID sensor. One method toward overcoming this issue is to use filters, but such method has generally proven to be difficult to implement and/or is not achieving the desired performance.

Another method, which has had general success in the marketplace, and developed by Ion Science Limited, is to use another electrode, e.g., a fence electrode, between the sensing electrode and the counter electrode to "block" the leak current from reaching the sense electrode, thus essentially making the leak current zero or close to zero. This method is generally described and illustrated in U.S. Pat. No. 7,046,012. More specifically, as described in this patent, the sensing electrode is positioned proximate to the lamp window while the counter electrode is positioned distal from the lamp window, and the fence electrode is positioned between the sensing electrode and the counter electrode. In practice, electrical potential is applied to each of the electrodes with the electrical potential applied to the fence electrode being equal to, or substantially equal to, the electrical potential applied to the sensing electrode, with such electrical potential being different from the electrical potential applied to the counter electrode, such that a voltage differential is defined between the sensing electrode and the counter electrode. With the electrical potentials applied, the current from the counter electrode to the sensing electrode is measured, which is essentially equal to the plasma/ionic current.

The foregoing method, however, has some disadvantages. More specifically, as the foregoing method essentially "blocks" the leak current, it does not measure the leak current, which measurement has its advantages. For instance, measuring or monitoring the leak current would provide information about the presence and amount of humidity and would also provide information regarding the condition of the PID sensor itself, for example, contamination within the PID sensor, or excessive drift due to the contamination such that a user may be alerted to perform necessary maintenance to the PID sensor based on such measurement.

As a result of the foregoing, certain individuals would appreciate further improvements in PIDs and the operation of same.

BRIEF SUMMARY

Accordingly, the present disclosure provides an improved PID.

In an embodiment, the present disclosure provides a sensor for detecting small concentrations of volatile organic compounds in ambient air that includes a lamp assembly and a gas sampling chamber assembly. The lamp assembly has a lamp housing and a window. The window is connected to the lamp housing. The gas sampling chamber assembly has an ionization chamber and an electrode assembly. The ionization chamber is defined by at least one wall having first and second ends. The at least one wall is formed of a hydrophobic, non-conductive material. The first end of the ionization chamber is operatively associated with the window to allow ultra-violet light to enter the ionization chamber from the lamp housing via the window. The electrode assembly comprises a sensing electrode, a counter electrode, at least one auxiliary electrode and circuitry. The electrodes are positioned within the ionization chamber and are separated from one another along the at least one wall. The circuitry is configured to apply a voltage difference to the sensing and counter electrodes to create an electric field across the electrodes, control an electrical potential of the at least one auxiliary electrode to be substantially equal to an electrical potential of the counter electrode, measure/estimate a current at the sensing electrode and at the at least one auxiliary electrode, determine a difference between the current at the sensing electrode and the current at the at least one auxiliary electrode, and correct the current at the sensing electrode by using the difference.

In an embodiment, the present disclosure provides the sensor where the circuitry is configured to apply the voltage difference to the sensing and counter electrodes by controlling electrical potentials of the sensing and counter electrodes to be substantially different such that the electrical potential of the at least one auxiliary electrode is substantially different from the electrical potential of the sensing electrode.

In an embodiment, the present disclosure provides the sensor where the circuitry has at least one circuit which measures/estimates the current at the sensing electrode and the current at the at least one auxiliary electrode, and where the circuitry has a signal processor that determines the difference.

In an embodiment, the present disclosure provides the sensor where the lamp housing is defined by at least one wall and has an end, the window being connected to the end of the lamp housing, and where the gas sampling chamber assembly further has a membrane, the membrane being operatively associated with the second end of the at least one wall of the ionization chamber to close off the second end of the ionization chamber.

In an embodiment, the present disclosure provides the sensor where the sensing electrode is positioned proximate to, or in contact with, the window, where the counter electrode is positioned proximate to the membrane, and where the at least one auxiliary electrode is positioned between the sensing and counter electrodes.

In an embodiment, the present disclosure provides the sensor where the sensing electrode is configured to allow ultra-violet light to enter the ionization chamber from the lamp housing via the window.

In an embodiment, the present disclosure provides the sensor where the sensing electrode is configured to collect electrons present on the at least one wall of the ionization chamber due to ultra-violet light therein ionizing gas molecules that have entered the ionization chamber through the membrane.

In an embodiment, the present disclosure provides the sensor where the counter electrode is configured to allow gas to enter the ionization chamber.

In an embodiment, the present disclosure provides the sensor where the counter electrode is configured to collect cations present within the ionization chamber due to ultra-violet light therein ionizing gas molecules that have entered the ionization chamber through the membrane.

In an embodiment, the present disclosure provides the sensor where the at least one auxiliary electrode is configured to not span across the ionization chamber.

In an embodiment, the present disclosure provides the sensor where the at least one auxiliary electrode is configured to be one of generally flush with, protrude beyond, or recessed from an inner surface of the at least one wall of the ionization chamber.

In an embodiment, the present disclosure provides the sensor where the at least one wall of the lamp housing is formed of glass, and where the window is formed of salt crystals.

In an embodiment, the present disclosure provides the sensor where the membrane is formed of a porous material.

In an embodiment, the present disclosure provides the sensor where the lamp housing may contain a low-pressure inert gas.

In an embodiment, the present disclosure provides a method of detecting small concentrations of volatile organic compounds in ambient air, where the method comprises the steps of: (a) providing a sensor having a lamp assembly and a gas sampling chamber assembly which is operatively associated with the lamp assembly, the gas sampling chamber assembly having an ionization chamber and an electrode assembly, the electrode assembly comprising a sensing electrode, a counter electrode, and at least one auxiliary electrode, the electrodes being positioned within the ionization chamber; (b) applying a voltage difference to the sensor and counter electrodes to create an electric field across the electrodes; (c) controlling an electrical potential of the at least one auxiliary electrode to be substantially equal to an electrical potential of the counter electrode; (d) measuring/estimating a current at the sensing electrode and at the at least one auxiliary electrode; (e) determining a difference between the current at the sensing electrode and the current at the at least one auxiliary electrode; and (f) correcting the current at the sensing electrode by using the difference.

In an embodiment, the present disclosure provides the method where the lamp assembly has a lamp housing and a window, the window being connected to the lamp housing, where the ionization chamber is defined by at least one wall having first and second ends, the at least one wall being formed of a hydrophobic, non-conductive material, the first end of the ionization chamber being operatively associated with the window to allow ultra-violet light to enter the ionization chamber from the lamp housing via the window, the electrodes being separated from one another along the at least one wall of the ionization chamber.

In an embodiment, the present disclosure provides the method where the gas sampling chamber further has a membrane, the membrane being operatively associated with the second end of the at least one wall of the ionization chamber to close off the second end of the ionization chamber, wherein the sensing electrode is positioned proximate to, or in contact with, the window, wherein the counter electrode is positioned proximate to the membrane, and wherein the at least one auxiliary electrode is positioned between the sensing and counter electrodes.

In an embodiment, the present disclosure provides the method where the electrode assembly further comprises circuitry, the circuitry being configured to perform steps (b) through (f).

In an embodiment, the present disclosure provides the method where the circuitry has at least one circuit which performs step (d), and where the circuitry has a signal processor that performs step (e).

In an embodiment, the present disclosure provides a sensor for detecting small concentrations of volatile organic compounds in ambient air that includes a lamp assembly and a gas sampling chamber assembly. The lamp assembly has a lamp housing and a window. The window is connected to the lamp housing. The gas sampling chamber assembly has an ionization chamber and an electrode assembly. The ionization chamber is defined by at least one wall having first and second ends. The at least one wall is formed of a hydrophobic, non-conductive material. The first end of the ionization chamber is operatively associated with the window to allow ultra-violet light to enter the ionization chamber from the lamp housing via the window. The electrode assembly comprises a sensing electrode, a counter electrode, at least one auxiliary electrode and circuitry. The electrodes are positioned within the ionization chamber and are separated from one another along the at least one wall. The circuitry is configured to apply a voltage difference to the sensing and counter electrodes to create an electric field across the electrodes, control an electrical potential of the at least one auxiliary electrode to be substantially different from an electrical potential of each of the sensing and counter electrodes, measure/estimate a current at the sensing electrode and at the at least one auxiliary electrode, determine a difference between the current at the sensing electrode and the current at the at least one auxiliary electrode, and correct the current at the sensing electrode by using the difference.

BRIEF DESCRIPTION OF THE DRAWINGS

The present disclosure is illustrated by way of example and not limited in the accompanying figures in which like reference numerals indicate similar elements and in which.

DETAILED DESCRIPTION

Figure 1:
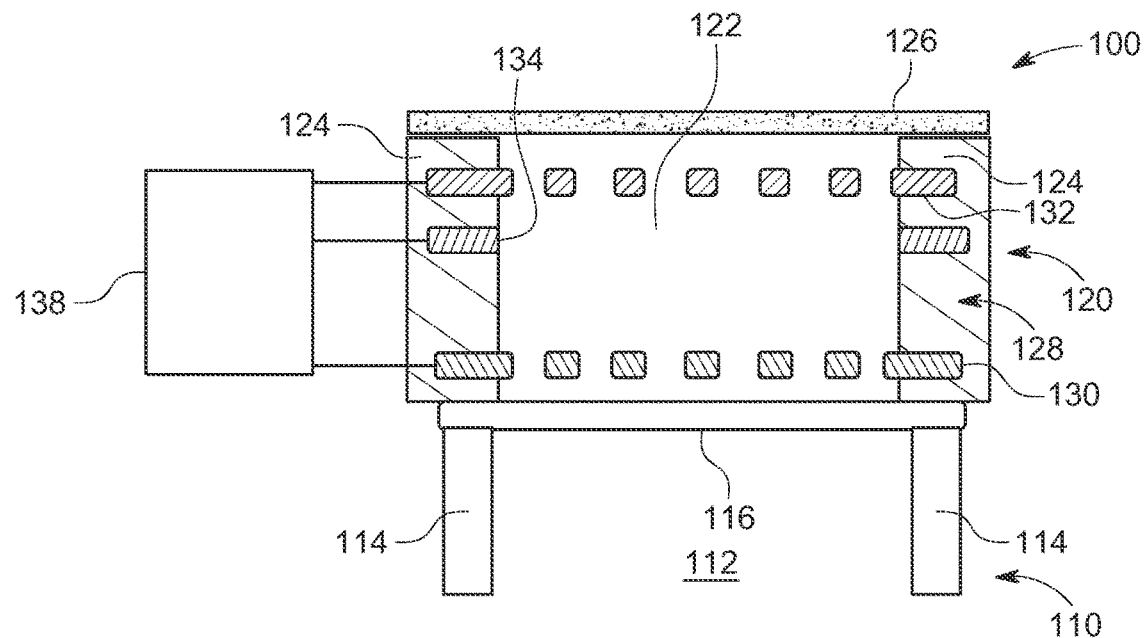
FIG. 1 illustrates a schematic representation of a photoionization detector including an auxiliary electrode according to a first embodiment.

While the disclosure may be susceptible to embodiment in different forms, there is shown in the drawings, and herein will be described in detail, specific embodiments with the understanding that the present disclosure is to be considered an exemplification of the principles of the disclosure and is not intended to limit the disclosure to that as illustrated and described herein. Therefore, unless otherwise noted, features disclosed herein may be combined to form additional combinations that were not otherwise shown for purposes of brevity. It will be further appreciated that in some embodiments, one or more elements illustrated by way of example in a drawing(s) may be eliminated and/or substituted with alternative elements within the scope of the disclosure.

Contrary to the prior art PIDs and operation methods used, as described above, the current disclosure handles the issue with an alternative configuration and method, which alternative configuration and method not only provides a plasma/ionic current, but also provides further advantages as will be explained in further detail hereinbelow. Instead of blocking the leak current, the method of the present disclosure includes: (a) measuring the total current that passes the sensing electrode; (b) using an auxiliary electrode to either directly measure or estimate the leak current; and (c) subtracting the leak current from the total plasma/ionic current to obtain the accurate plasma/ionic current value.

Attention is directed to FIG. 1 and a first embodiment of a photoionization detector ("PID") 100. PID 100 includes a lamp assembly 110 and a gas sampling chamber assembly 120 which are operatively associated with one another.

The lamp assembly 110 includes a lamp housing 112 defined by one or more walls 114. A window 116 is provided at an end of the walls 114 (illustrated in FIG. 1 as being at a top end of the walls 114). The walls 114 are preferably formed of glass and the window is preferably formed of salt crystals (e.g., $MgF_2$, $LiF$, $CaF_2$, $BaF_2$) as they allow for the transmission of the vacuum UV light required to ionize target compounds. The lamp housing 112 may be filled with a low-pressure inert gas such as He, Ar Kr or Xe, as is known to those skilled in the art.

The gas sampling chamber assembly 120 includes an ionization chamber 122 that is defined by one or more walls 124. The walls 124 are preferably formed of a hydrophobic/waterproof/water repellant, insulative (non-conductive) material, such as Teflon. The window 116 of the lamp assembly 110 is connected to or operatively associated with a first end of the walls 124 (illustrated in FIG. 1 as being at a lower end of the walls 124) in order to close off a first end of the ionization chamber 122 (illustrated in FIG. 1 as being a lower end of the ionization chamber 122).

The gas sampling chamber assembly 120 includes a membrane 126 that is connected to or operatively associated with a second end of the walls 124 (illustrated in FIG. 1 as being at an upper end of the walls 124) in order to close off a second end of the ionization chamber 122 (illustrated in FIG. 1 as being an upper end of the ionization chamber 122). The membrane 126 is preferably formed of a porous material, such as e-PTFE, which allows gas to be sampled to enter the ionization chamber 122 via the membrane 126, but acts to block dust, water, and other particulates (collectively contaminants).

The gas sampling chamber assembly 120 includes an electrode assembly 128 having a first electrode 130, a second electrode 132, a third electrode 134, and circuitry 138. Each of the electrodes 130, 132, 134 are housed within the ionization chamber 122 (between the window 116 and the membrane 126) and are preferably held in place by being operatively associated with the walls 124.

The first electrode 130 is preferably a sensing electrode. The first/sensing electrode 130 is positioned between the membrane 126 and the window 116. The first/sensing electrode 130 is preferably positioned to be in contact with, or in close proximity to, the window 116. The first/sensing electrode 130 is configured to allow photons (e.g., vacuum UV light) passing through the window 116 from the lamp housing 112 to pass into the ionization chamber 122. The first/sensing electrode 130 is further configured to collect electrons present on the walls 124 of the ionization chamber 122 due to vacuum UV light therein ionizing the gas molecules that have entered the ionization chamber 122 through the membrane 126.

The second electrode 132 is preferably a counter electrode. The second/counter electrode 132 is positioned between the membrane 116 and the first/sensing electrode 130. The second/sensing electrode is preferably positioned to be in close proximity to the membrane 126. The second/counter electrode 132 is configured to allow gas to enter the ionization chamber 122. The second/counter electrode 132 is further configured to collect cations present within the ionization chamber 122 due to vacuum UV light therein ionizing the gas molecules that have entered the ionization chamber 122 through the membrane 126.

The third electrode 134 is preferably an auxiliary electrode. The third/auxiliary electrode 134 is positioned between the first/sensing electrode 130 and the second/counter electrode 132. The third/auxiliary electrode 134 is preferably configured to not span across the ionization chamber 122, but rather is preferably configured to be generally flush with an inner surface of the walls 124 so as to minimize interferences with the ionized particles within the ionization chamber 122 but may also either protrude beyond the inner surface of the walls 124 and into the ionization chamber 122 or be recessed from the inner surface of the walls 124.

The circuitry 138 is connected to each of the first, second and third electrodes 130, 132, 134. The circuitry 138 is of a type that is known and the function of the circuitry 138 will be discussed in further detail hereinbelow.

In operation, the circuitry 138 provides electrical potential to each of the first/sensing electrode 130, the second/counter electrode 132 and the third/auxiliary electrode 134. The electrical potential provided to the first/sensing electrode 130 and the second/counter electrode 132 is substantially different, such that a desired voltage is defined between the first/sensing electrode 130 and the second/counter electrode 132. Furthermore, the electrical potential provided to the third/auxiliary electrode 134 is substantially equal to, or equal to, the electrical potential provided to the second/counter electrode 132, such that no voltage (or a negligible voltage) is defined between the third/auxiliary electrode 134 and the second/counter electrode 132. For reference, "substantially equal" is intended to be an amount that is typically measured in millivolts, e.g., approximately less than 1 Volt, whereas "substantially different" is intended to be an amount that is measured in Volts, e.g., approximately 10 Volts or greater. In a preferred embodiment, "substantially different" is intended to be an amount that is 100 Volts or greater.

Figure 2:
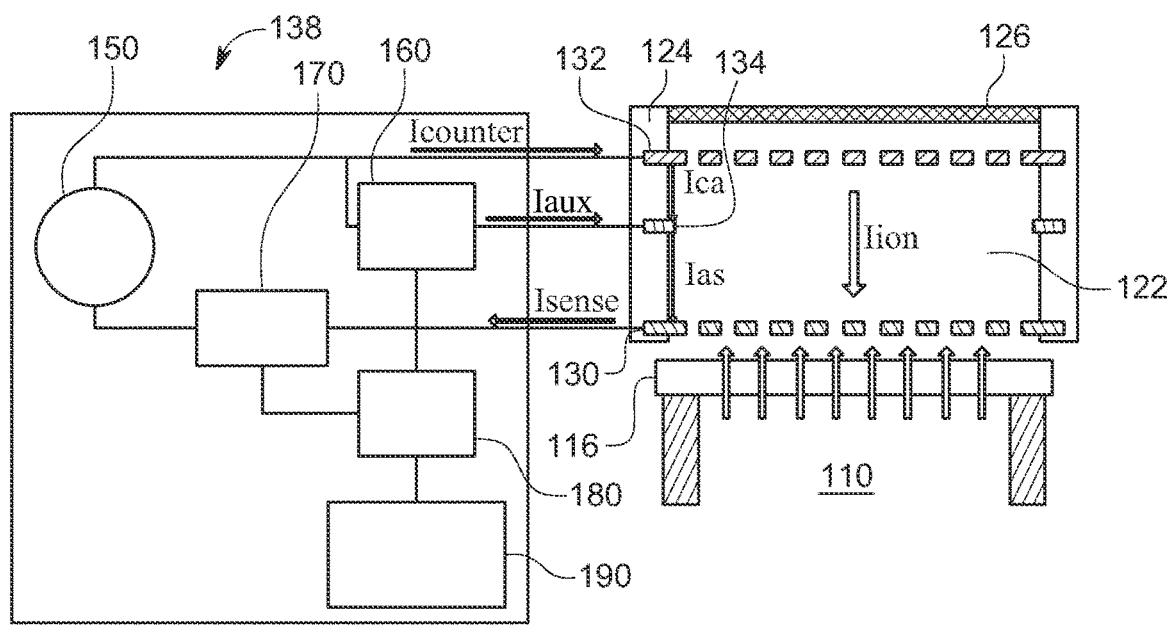
FIG. 2 illustrates a schematic representation of the photoionization detector as illustrated in FIG. 1 with further detail illustrating the circuitry and the currents being generated.

FIG. 2 illustrates how the circuit 138 operates. The circuit 138 effectively measures ionization current ($I_{ion}$) within the ionization chamber 122. A power source 150 provides a high voltage (a substantially different voltage) between the second/counter electrode 132 and the first/sensing electrode 130 that ionizes gas present in the ionization chamber 122 and causes current flow between the electrodes 130, 132. The measured current ($I_{sense}$) at the first/sensing electrode 130 is typically proportional to the gas concentration in the sensing chamber 122. Due to an accumulated moisture on the walls 124, there is a parasitic leak current flowing from the second/counter electrode 132 to the first/sensing electrode 130 introducing an error in the measured current ($I_{sense}$) at the first/sensing electrode 130. A method to compensate for a current related to accumulated moisture employs the third/auxiliary electrode 134, which is placed between the second/counter electrode 132 and the first/sensing electrode 130.

The third/auxiliary electrode 134 is kept at the same electrical potential (a substantially equal voltage) as the second/counter electrode 132 in reference to the first/sensing electrode 130. Since voltage potential between the second/counter electrode 132 and the third/auxiliary electrode 134 is zero or negligible, there is no current ($I_{ca}$) flow (or only negligible current ($I_{ca}$) flow) between the second/counter electrode 132 and the third/auxiliary electrode 134 via moisture condensed on the walls 124 between the second/counter electrode 132 and the third/auxiliary electrode 134. Virtually all the current ($I_{as}$) induced by an electrical potential difference between the third/auxiliary electrode 134 and the first/sensing electrode 130 due to the moisture accumulation is flowing via the third/auxiliary electrode 134. The current ($I_{aux}$) flowing via the third/auxiliary electrode 134 can be measured with a measurement circuit 160 which can be as simple as a voltage drop measuring device on a sensing resistor. Whatever method is employed for an implementation of the measurement circuit 160, it should provide as little voltage drop on the device itself to ensure that the potentials of the second/counter electrode 132 and the third/auxiliary electrode 134 are very close to each other if not identical (substantially equal).

Another current measurement circuit 170 measures the current ($I_{sense}$) flowing via the first/sensing electrode 130. Ionization current ($I_{ion}$) proportional to the target gas concentration in the sensing chamber 122 can be derived by subtracting the current ($I_{aux}$) flowing via the third/auxiliary electrode 134 from the current ($I_{sense}$) flowing via the first/sensing electrode 130. Circuit 180 is a signal processor that calculates the difference between the results from measurement circuit 160 and measurement circuit 170. This process of subtraction can be accomplished via several different ways. One method involves current subtraction via dedicated analog electronic circuit. Another method would require for sensed currents ($I_{sense}$ and $I_{aux}$) to be digitized (after amplification) with an analog-to-digital converter connected to a microprocessor. The microprocessor would subtract the values to derive ionization current ($I_{ion}$) value free of error caused by current flow due to moisture accumulation. The results from signal processor 180 can be sent to one or more output devices 190, which may include a digital display, and/or visual/audible alarms, and/or an interface to other control systems.

With the electrical potentials applied, the total current ($I_{sense}$) through the first/sensing electrode 130 is measured. Condensation/humidity generally occurs along the walls 124 of the ionization chamber 122 as water will adhere to the walls 124 (or more likely to contaminants that have collected along the walls 124 as the walls 124 are preferably formed of a water resistant/water repellant material). Such condensation/humidity will create a leak current within the ionization chamber 122, which leak current might lead to a false reading and/or misinterpretation of the plasma/ionic current ($I_{ion}$). Since electric potential difference between the second/counter electrode 132 and the third/auxiliary electrode 134 is zero or close to zero (substantially equal), there is no current flow between these electrodes and all leakage current is flowing through the third/auxiliary electrode 134 to the first/sensing electrode 130. Thus, in order to compensate for same, the leak current is measured (or estimated) as $I_{aux}$ flowing through the third/auxiliary electrode 134 to the first/sensing electrode 130. Once the $I_{aux}$ and $I_{sense}$ are measured/estimated, the following formula(s) can be used to determine the true plasma/ionic current ($I_{ion}$) from the second/counter electrode 132 to the first/sensing electrode 130. The circuit 138 thus corrects the current at the first/sensing electrode 130 to determine the true plasma/ionic current ($I_{ion}$) using the difference.

$$I_{ion} = I_{sense} - I_{aux} \quad \text{(Equation 1)}$$

In addition to providing a true plasma/ionic current ($I_{ion}$) from the second/counter electrode 132 to the first/sensing electrode 130, the foregoing configuration/method further provides information regarding humidity levels and possible contaminants within the ionization chamber 122, which further information is not provided/possible based on the configuration/method as taught in U.S. Pat. No. 7,046,012 or with any other known design.

More specifically, as the leak current ($I_{aux}$) is actively measured, this measurement can be used to determine the humidity level where the PID 100 is located. Furthermore, if the PID 100 is provided in an area where the humidity level is known to be low or zero, yet the humidity level is determined to be something other than low or zero, the operator can then quickly deduce that the PID 100 is not operating properly, likely due to the presence of contaminants that have entered the ionization chamber 122 and were deposited on walls 124 contributing to a leakage current from third/auxiliary electrode 134 to the first/sensing electrode 130. If the PID 100 is therefore not operating properly, the operator will know that any readings generated by the PID 100 are likely not accurate and cannot be trusted, such that the PID 100 should then be cleaned/repaired/replaced as appropriate. Still further, if the PID 100 is provided in an area where the humidity level is not known, the humidity level determined by one PID 100 may be compared to the humidity levels determined by other like PIDs 100 in the same vicinity. If the humidity level determined by the one PID 100 is off compared to the humidity levels determined by the other like PIDs 100, then the operator can again quickly deduce that the PID 100 is not operating properly, likely due to the presence of contaminants that have entered the ionization chamber 122. The PID 100 should then be cleaned/repaired/replaced as appropriate.

Figure 3:
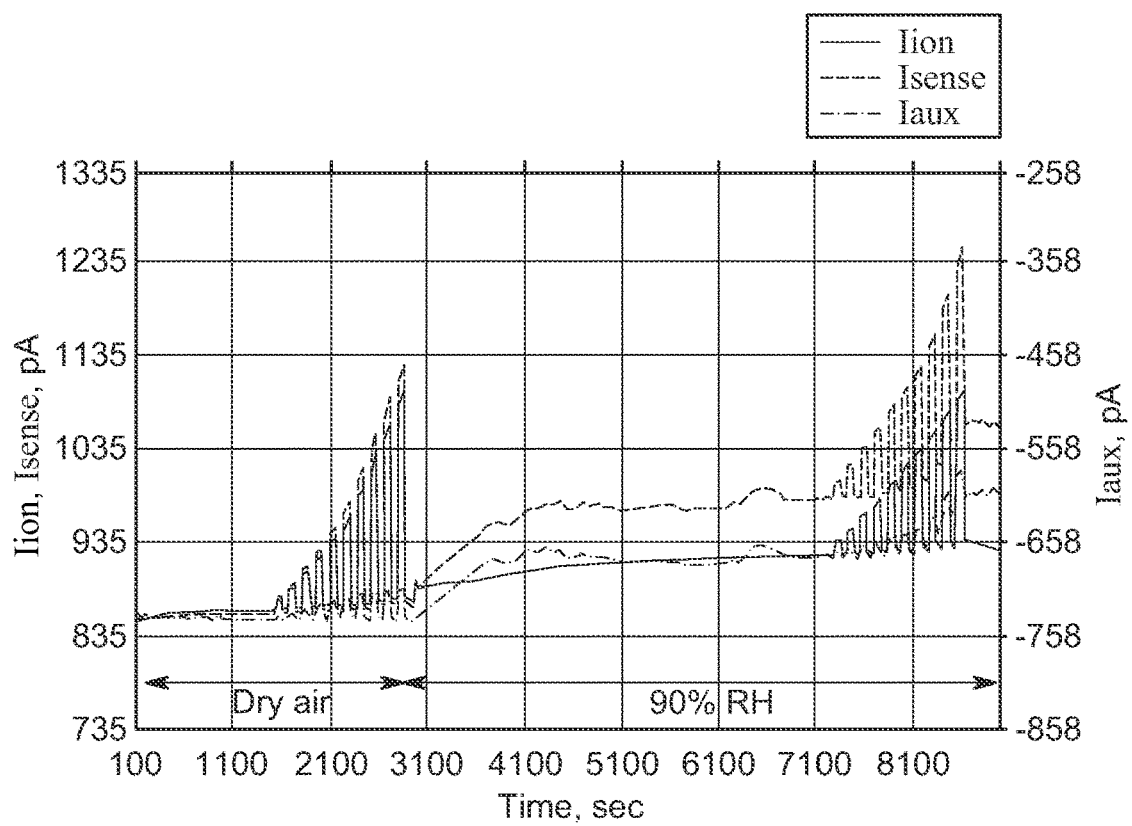
FIG. 3 illustrates a graphical representation of sensor responses to 0.25 ppm step changes in isobutylene gas concentrations under 0% and 90% relative humidity (RH) using the photoionization detector of the first embodiment.

FIG. 3 illustrates test results of a prototype sensor and drive circuitry built according to FIGS. 1 and 2. The sensor was exposed to isobutylene gas of increasing gas concentrations under 0% and 90% relative humidity ("RH"), respectively. Under each RH, the gas concentration was increased by 0.25 ppm each time and the exposure time was about 60 seconds at each gas concentration. The incremental gas concentrations were separated by pure air purge. When air was switched from dry air to 90% RH, the sensor's baseline output was allowed to stabilize and then the step gas concentrations applied. The moisture induced wall current ($I_{aux}$) was measured along sense electrode current ($I_{sense}$) and the gas ionization current ($I_{ion}$) was calculated by subtracting the wall current ($I_{aux}$) from the sense electrode current ($I_{sense}$) according to Equation 1. As shown in FIG. 3, the leak current ($I_{aux}$) very closely traces changes in the baseline of the sense electrode current ($I_{sense}$) after humid air was applied, and, by subtracting the leak current ($I_{aux}$), the ionization current ($I_{ion}$) follows about the same trend as the gas ionization current ($I_{ion}$) in dry air. This suggests a substantial reduction of the humidity effect on the sensor output through leak current compensation.

Figure 4:
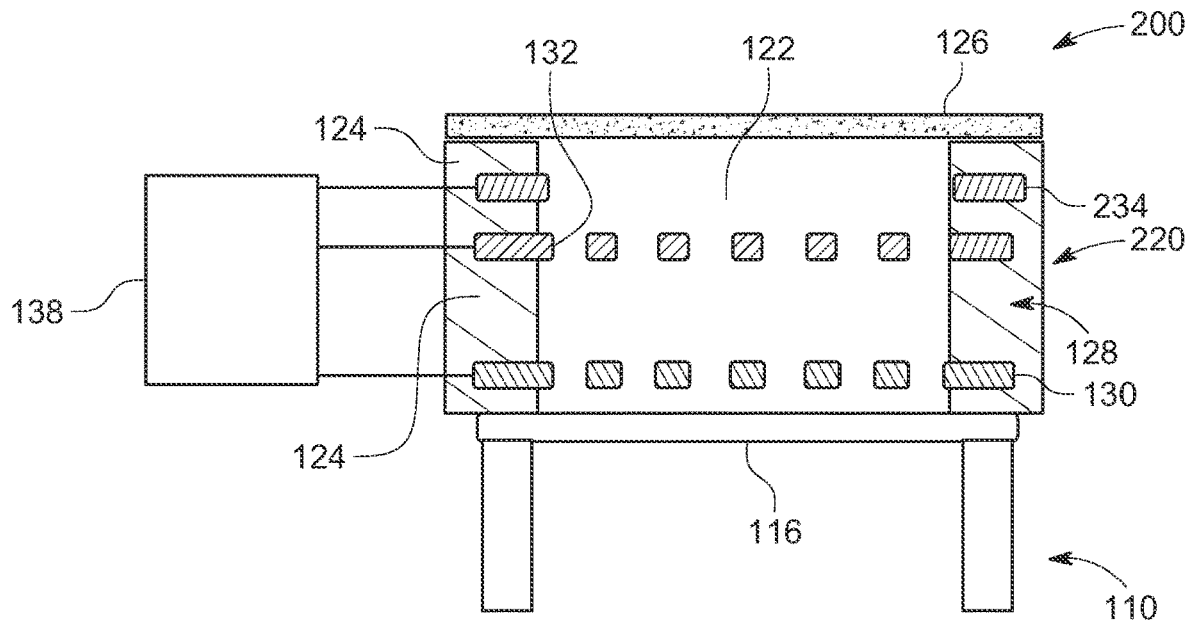
FIG. 4 illustrates a schematic representation of a photoionization detector including an auxiliary electrode according to a second embodiment.

Attention is directed to FIG. 4 and a second embodiment of a photoionization detector ("PID") 200. PID 200 includes the lamp assembly 110 (the lamp assembly of the second embodiment of the PID 200 is identical to the lamp assembly of the first embodiment of the PID 100 and, therefore, the description of same will not be repeated for brevity purposes) and a gas sampling chamber assembly 220 which are operatively associated with one another.

The gas sampling chamber assembly 220 includes the ionization chamber 122, the walls 124 and the membrane 126 (the ionization chamber, walls, and membrane of the second embodiment of the PID 200 are identical to the ionization chamber, walls, and membrane of the first embodiment of the PID 100 and, therefore, the description of same will not be repeated for brevity purposes).

The gas sampling chamber assembly 220 includes an electrode assembly 228 having the first electrode 130, the second electrode 132, a third electrode 234 and circuitry 138 (the first electrode, the second electrode and the circuitry of the second embodiment of the PID 200 are identical to the first electrode, the second electrode and the circuitry of the first embodiment of the PID 100 and, therefore, the description of same will not be repeated for brevity purposes). The third electrode 234 is housed within the ionization chamber 122 (between the window 116 and the membrane 126) and is preferably held in place by being operatively associated with the walls 124.

The third electrode 234 is preferably an auxiliary electrode. The third/auxiliary electrode 234 is positioned between the membrane 126 and the second/counter electrode 132. The third/auxiliary electrode 234 is preferably configured to not span across the ionization chamber 122, but rather is preferably configured to be generally flush with an inner surface of the walls 124 so as to minimize interferences with the ionized particles within the ionization chamber 122 but may also either protrude beyond the inner surface of the walls 124 and into the ionization chamber 122 or be recessed from the inner surface of the walls 124.

In addition to being connected to the first/sensing electrode 130 and the second/counter electrode 132, the circuitry 138 is further connected to the third/auxiliary electrode 234.

Operation of the PID 200 works in a similar manner as operation of the PID 100 except the third/auxiliary electrode 234 is held at a substantially different potential from the second/counter electrode 132 and PID 200 provides almost the same advantages as PID 100. Because of the voltage differential (substantially different) between the second/counter electrode 132 and the third/auxiliary electrode 234, there is a current ($I_{aux}$) that passes the third/auxiliary electrode 234 and this current ($I_{aux}$) is used to correct the current ($I_{sense}$) flowing via the first/sensing electrode 130. Depending on the voltage applied between the third/auxiliary electrode 234 and the second/counter electrode 132, electrode spacings, and the geometry of the electrode stack, calculated leak current may be a ratio of the current ($I_{aux}$) flowing via the third/auxiliary electrode 134 and accurate correction can still be performed. The current ($I_{aux}$) flowing via the third/auxiliary electrode 134 is also an indication of the condition of the sensor as described earlier.

In each of the embodiments described hereinabove, the first/sensing electrode 130 is positioned to be in contact with, or in close proximity to, the window 116, whereas the second/counter electrode 132 is positioned to be distal from the window 116. However, it should be noted that in alternative embodiments, the position of the first/sensing electrode 130 and the second/counter electrode 132 could be switched, but such a configuration is not preferred as it is not desirable to have UV light shining on the second/counter electrode 132 and thus causes a high baseline out associated with photocurrent.

In an alternative embodiment, the configuration of the PID 100 and 200 could be modified to provide more than one of the third/auxiliary electrodes 134, 234.

While particular embodiments are illustrated in and described with respect to the drawings, it is envisioned that those skilled in the art may devise various modifications without departing from the spirit and scope of the appended claims. It will therefore be appreciated that the scope of the disclosure and the appended claims is not limited to the specific embodiments illustrated in and discussed with respect to the drawings and that modifications and other embodiments are intended to be included within the scope of the disclosure and appended drawings. Moreover, although the foregoing descriptions and the associated drawings describe example embodiments in the context of certain example combinations of elements and/or functions, it should be appreciated that different combinations of elements and/or functions may be provided by alternative embodiments without departing from the scope of the disclosure and the appended claims.

We claim:

1. A sensor for detecting small concentrations of volatile organic compounds in ambient air, the sensor comprising:
 a lamp assembly having a lamp housing and a window, the window being connected to the lamp housing;
 a gas sampling chamber assembly having an ionization chamber and an electrode assembly,
  the ionization chamber being defined by at least one wall having first and second ends, the at least one wall being formed of a hydrophobic, non-conductive material, the first end of the ionization chamber being operatively associated with the window to allow ultra-violet light to enter the ionization chamber from the lamp housing via the window,
  the electrode assembly comprising a sensing electrode, a counter electrode, at least one auxiliary electrode, and circuitry, with the sensing, counter, and at least one auxiliary electrodes being positioned within the ionization chamber and being separated from one another along the at least one wall, wherein the at least one auxiliary electrode is positioned between the sensing electrode and counter electrode, the circuitry configured to
   apply a voltage difference to the sensing and counter electrodes to create an electric field across at least the sensing and counter electrodes,
   control an electrical potential of the at least one auxiliary electrode to be substantially equal to an electrical potential of the counter electrode,
   measure/estimate a current at the sensing electrode and at the at least one auxiliary electrode,
   determine a difference between the current at the sensing electrode and the current at the at least one auxiliary electrode, and
   correct the current at the sensing electrode by using the difference.

2. The sensor as defined in claim 1, wherein the circuitry is configured to apply the voltage difference to the sensing and counter electrodes by controlling electrical potentials of the sensing and counter electrodes to be substantially different such that the electrical potential of the at least one auxiliary electrode is substantially different from the electrical potential of the sensing electrode.

3. The sensor as defined in claim 1, wherein the circuitry has at least one circuit which measures/estimates the current at the sensing electrode and the current at the at least one auxiliary electrode, and wherein the circuitry has a signal processor that determines the difference.

4. The sensor as defined in claim 1, wherein the lamp housing is defined by at least one wall and has an end, the window being connected to the end of the lamp housing, and wherein the gas sampling chamber assembly further has a membrane, the membrane being operatively associated with the second end of the at least one wall of the ionization chamber to close off the second end of the ionization chamber.

5. The sensor as defined in claim 4, wherein the sensing electrode is positioned proximate to, or in contact with, the window, wherein the counter electrode is positioned proximate to the membrane, and wherein the at least one auxiliary electrode is positioned between the sensing and counter electrodes.

6. The sensor as defined in claim 5, wherein the sensing electrode is configured to allow the ultra-violet light to enter the ionization chamber from the lamp housing via the window.

7. The sensor as defined in claim 5, wherein the sensing electrode is configured to collect electrons present on the at least one wall of the ionization chamber due to the ultra-violet light therein ionizing gas molecules that have entered the ionization chamber through the membrane.

8. The sensor as defined in claim 5, wherein the counter electrode is configured to allow gas to enter the ionization chamber.

9. The sensor as defined in claim 5, wherein the counter electrode is configured to collect cations present within the ionization chamber due to the ultra-violet light therein ionizing gas molecules that have entered the ionization chamber through the membrane.

10. The sensor as defined in claim 5, wherein the at least one auxiliary electrode is configured to not span across the ionization chamber.

11. The sensor as defined in claim 10, wherein the at least one auxiliary electrode is configured to be one of generally flush with, protrude beyond, or recessed from an inner surface of the at least one wall of the ionization chamber.

12. The sensor as defined in claim 4, wherein the at least one wall of the lamp housing is formed of glass, and wherein the window is formed of salt crystals.

13. The sensor as defined in claim 4, wherein the membrane is formed of a porous material.

14. The sensor as defined in claim 1, wherein the lamp housing may contain a low-pressure inert gas.

15. A method of detecting small concentrations of volatile organic compounds in ambient air, the method comprising the steps of:
 (a) providing a sensor having a lamp assembly and a gas sampling chamber assembly which is operatively associated with the lamp assembly, the gas sampling chamber assembly having an ionization chamber and an electrode assembly, the electrode assembly comprising a sensing electrode, a counter electrode, and, at least one auxiliary electrode, and the sensing, counter, and at least one auxiliary electrodes being positioned within the ionization chamber and being separated from one another along at least one wall, wherein the at least one auxiliary electrode is positioned between the sensing electrode and counter electrode;
 (b) applying a voltage difference to the sensor and counter electrodes to create an electric field across at least the sensor and counter electrodes;
 (c) controlling an electrical potential of the at least one auxiliary electrode to be substantially equal to an electrical potential of the counter electrode;
 (d) measuring/estimating a current at the sensing electrode and at the at least one auxiliary electrode;
 (e) determining a difference between the current at the sensing electrode and the current at the at least one auxiliary electrode; and
 (f) correcting the current at the sensing electrode by using the difference.

16. The method as defined in claim 15, wherein the lamp assembly has a lamp housing and a window, the window being connected to the lamp housing, wherein the ionization chamber is defined by the at least one wall having first and second ends, the at least one wall being formed of a hydrophobic, non-conductive material, the first end of the ionization chamber being operatively associated with the window to allow ultra-violet light to enter the ionization chamber from the lamp housing via the window, the sensing, counter, and at least one auxiliary electrodes being separated from one another along the at least one wall of the ionization chamber.

17. The method as defined in claim 16, wherein the gas sampling chamber assembly further has a membrane, the membrane being operatively associated with the second end of the at least one wall of the ionization chamber to close off the second end of the ionization chamber, wherein the sensing electrode is positioned proximate to, or in contact with, the window, wherein the counter electrode is positioned proximate to the membrane, and wherein the at least one auxiliary electrode is positioned between the sensing and counter electrodes.

18. The method as defined in claim 15, wherein the electrode assembly further comprises circuitry, the circuitry being configured to perform steps (b) through (f).

19. The method as defined in claim 18, wherein the circuitry has at least one circuit which performs step (d), and wherein the circuitry has a signal processor that performs step (e).

20. A sensor for detecting small concentrations of volatile organic compounds in ambient air, the sensor comprising:
  a lamp assembly having a lamp housing and a window, the window being connected to the lamp housing;
  a gas sampling chamber assembly having an ionization chamber and an electrode assembly,
    the ionization chamber being defined by at least one wall having first and second ends, the at least one wall being formed of a hydrophobic, non-conductive material, the first end of the ionization chamber being operatively associated with the window to allow ultra-violet light to enter the ionization chamber from the lamp housing via the window,
    the electrode assembly comprising a sensing electrode, a counter electrode, at least one auxiliary electrode and circuitry, the sensing, counter, and at least one auxiliary electrodes being positioned within the ionization chamber and being separated from one another along the at least one wall, wherein the at least one auxiliary electrode is positioned between the sensing electrode and counter electrode, the circuitry configured to
      apply a voltage difference to the sensing and counter electrodes to create an electric field across at least the sensing and counter electrodes,
      control an electrical potential of the at least one auxiliary electrode to be substantially different from an electrical potential of each of the sensing and counter electrodes,
      measure/estimate a current at the sensing electrode and at the at least one auxiliary electrode,
      determine a difference between the current at the sensing electrode and the current at the at least one auxiliary electrode, and
      correct the current at the sensing electrode by using the difference.

* * * * *